US006227201B1

(12) United States Patent
Ferko, III

(10) Patent No.: US 6,227,201 B1
(45) Date of Patent: May 8, 2001

(54) IMMOBILIZATION BACKBOARD AND BLANK FOR FORMING A BACKBOARD

(76) Inventor: Joseph G. Ferko, III, 412 Park Creek Rd., Pasadena, MD (US) 21122

(*) Notice: Subject to any disclaimer, the term of this patent is extended or adjusted under 35 U.S.C. 154(b) by 0 days.

(21) Appl. No.: 09/435,203
(22) Filed: Nov. 5, 1999
(51) Int. Cl.[7] ...................................................... A61B 19/00
(52) U.S. Cl. ................................ 128/869; 128/870; 5/628
(58) Field of Search ..................................... 128/845, 846, 128/869, 870; 5/625, 627, 628

(56) References Cited

U.S. PATENT DOCUMENTS 2,489,828 * 11/1949 Springer ..................................... 5/82
3,732,863 * 5/1973 Harrington ................................. 5/82
4,899,736 * 2/1990 Nesbitt ................................. 128/870

* cited by examiner

*Primary Examiner*—Michael A. Brown
(74) *Attorney, Agent, or Firm*—Roylance, Abrams, Berdo & Goodman, L.L.P.

(57) ABSTRACT

A backboard is formed from a cut blank defining a base and a top panel. The base has a generally rectangular shape with side panels coupled to the center panel by a fold line. The top panel is secured to the center panel of the base to increase the strength of the backboard. The top panel includes a center panel having a plurality of foldable arms which can be folded inwardly over a patient positioned on the backboard to restrain the patient on the backboard. The top panel also includes a pair of flaps that are folded along fold lines to form a head support for engaging the sides of a patient's head and preventing twisting or lateral movement of the patient's head. A securing device is placed around the backboard and the patient to restrain the patient and to assist in lifting the backboard.

44 Claims, 5 Drawing Sheets

IMMOBILIZATION BACKBOARD AND BLANK FOR FORMING A BACKBOARD

FIELD OF THE INVENTION

The present invention is directed to an immobilizing backboard for transporting a patient. More particularly the invention is directed to a disposable backboard assembled from a folded blank and to the blank for forming the backboard.

BACKGROUND OF THE INVENTION

Backboards are an essential piece of equipment for medical and emergency personnel for safely moving a patient in a manner to minimize the risk of spinal injury. Backboards and stretchers are also essential in transporting a patient in a manner that is convenient for the medical personnel and the most comfortable to the patient.

When a person has suffered a possible spinal or neck injury, the use of a standard stretcher is not suitable since the neck is not effectively immobilized. It is essential that the entire body be restrained from movement until the extent of the injuries are determined. To prevent movement of the neck and spine, a backboard is attached to the patient and a head immobilizing device is secured to the backboard.

The head immobilizing devices are known in the art for stabilizing an injured patient. One example of a head immobilizing device is disclosed in U.S. Pat. No. 5,944,016 to Ferko. This device is intended to be mounted to a rigid backboard to support a patient's head. The device includes a plurality of panels that are folded to support each side of a patient's head.

The backboards in common use today are rigid boards having handles or openings for gripping the board. The board must be sufficiently rigid to support the weight of the patient without buckling or folding. However, the board must also be sufficiently lightweight to avoid unnecessary weight being carried by the medical personnel or paramedics. It is desirable to manufacture the backboard to be compact as reasonably possible to minimize storage space.

Conventional backboards are often made from flat sheet material such as plywood, plastic or metal. The flat backboards usually have a number of openings around the edge for lifting and receiving straps to secure the patient to the board. Other backboards are made from molded plastic materials. Another form of backboard is made of metal and has number of pivotable supporting surfaces which can be placed around the patient while in the open position. The pivotable supporting surfaces are closed to slide beneath the patient so that the patient can be positioned on the backboard without lifting the patient from the ground.

The backboards and stretchers in common used today are expensive and intended for reuse. However, a patient is typically transported to a hospital on the backboard by emergency personnel so that the backboard remains with the patient until the patient is treated and removed from the board. The board must then be returned to the emergency personnel. The expense and bulk of the existing backboards limit the number of backboards which can be stored and carried by the emergency personnel.

Backboards have been made of inexpensive materials such as cardboard so that the backboard can be discarded after use. An example of a disposable board is disclosed in U.S. Pat. No. 4,584,729 to Roberts et al. This device includes a main panel and a cradle member having a pair of wings extending from the cradle. The wings are formed by fold lines on the cradle so that the wings can be raised to and the patient strapped in place.

Accordingly, there is a continuing need in the industry for an improved backboard.

SUMMARY OF THE INVENTION

The present invention is directed to a backboard and to a blank for forming a backboard. More particularly, the invention is directed to a backboard having a head stabilizing member coupled to the backboard.

Accordingly, a primary object of the invention is to provide a backboard that is produced from inexpensive materials and can be discarded after a single use.

Another object of the invention is to provide a blank which can be easily folded and shaped to form a rigid backboard that is sufficiently strong to support the weight of a patient.

A further object of the invention is to provide a backboard which can be stored in a substantially flat condition.

Still another object of the invention is to provide a rigid backboard formed from a corrugated cardboard.

Another object of the invention is to provide a disposable backboard having a head restraining device integrally formed with the backboard.

A further object of the invention is to provide an assembly including a first and a second blank for forming a backboard where the blanks can be cut by a single die cutting step.

Another object of the invention is to provide a backboard having at least one foldable arm attached to each side of the backboard, where the arms can be folded over the torso of a patient.

A further object of the invention is to provide a backboard having side edges and a plurality of arms hinged to the side edges for covering a patient and securing the patient to the board.

Still another object of the invention is to provide a backboard having a head restraining device that can be folded flat for easy storage.

Another object of the invention is to provide a belt having a buckle and at least one loop where the belt can be placed around the waist of a patient or around the backboard and the patient to restrain the patient and lift the backboard.

The objects and advantages of the invention are basically attained by providing a backboard support comprising a substantially planar base member having a rigid center panel with a longitudinal dimension, a first longitudinal end, a second longitudinal end, a first side edge, and second side edge. The base further has a first side panel pivotally coupled to the first side edge, and a second side panel pivotally coupled to the second side edge. A plurality of flexible arms are coupled to the planar base and are hinged thereto along each of the first and second side edges and have a length to overlie a patient on the support for securing the patient on the support.

The objects of the invention are further attained by providing a backboard support for carrying a patient, which comprises a planar base which has a longitudinal dimension with first and second longitudinal ends and first and second side edges, and a patient supporting panel which has a longitudinal dimension with a first and a second longitudinal end and a first and a second side edge. The patient supporting panel is coupled to the base. At least one arm is coupled to each of the first and second side edges of the patient supporting panel and is hinged thereto. The arms have a length for overlying a patient on the support.

The objects of the invention are also attained by providing an assembly for forming a backboard support comprising a first blank having a longitudinal dimension with longitudinal ends and first and second side edges; and a second blank having a center panel with a longitudinal dimension and having longitudinal ends and first and second side edges. At least one arm is coupled to each of the side edges of the center panel along a fold line.

These and other objects, advantages and salient features of the invention will become apparent from the following detailed description of the invention and the annexed drawings which form a part of this original disclosure.

BRIEF DESCRIPTION OF THE DRAWINGS

The following is a brief description of the drawings in which.

DETAILED DESCRIPTION OF THE INVENTION

Figure 1:
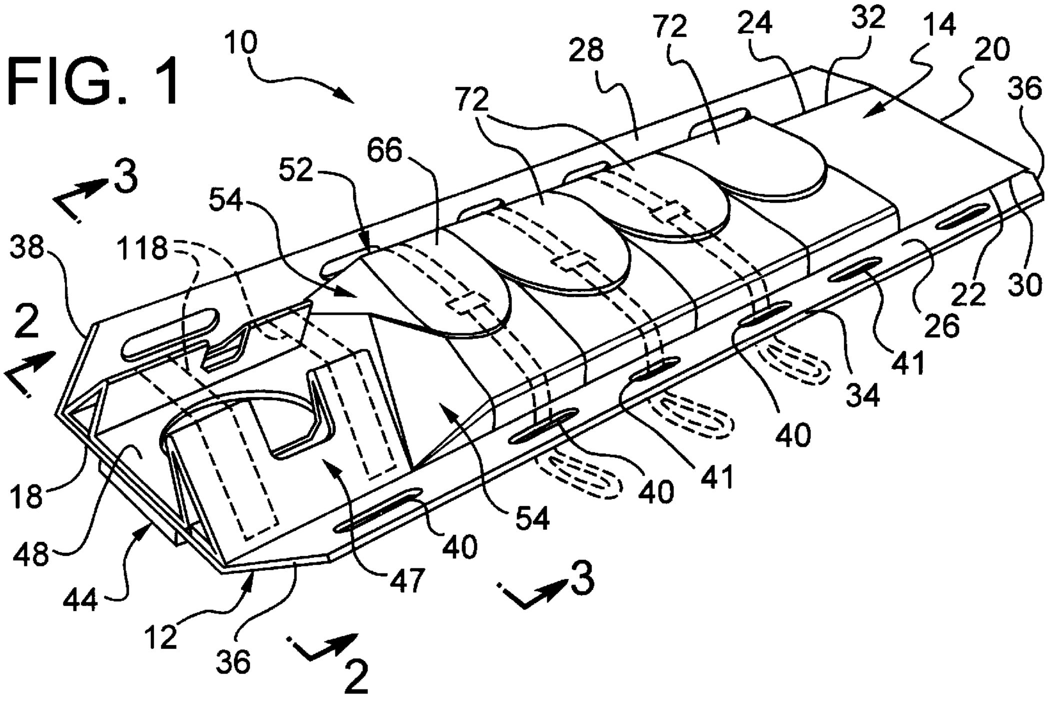
FIG. 1 is a perspective view of the backboard in a first embodiment of the invention.

The present invention is directed to a backboard that is lightweight and easy to handle. The backboard of the invention generally is made of a lightweight material such as corrugated cardboard, plastic or other materials. In preferred embodiments, the backboard is made of corrugated cardboard that has been coated with a water resistant or waterproofing material. Alternatively, the device can be made of plastic by suitable injection molding or thermoforming techniques as known in the art.

Referring to the drawings, the invention is directed to a backboard 10 having a base 12 and a top panel 14. The top panel 14 overlies and is attached to the base 12 as shown in FIG. 1.

Figure 4:
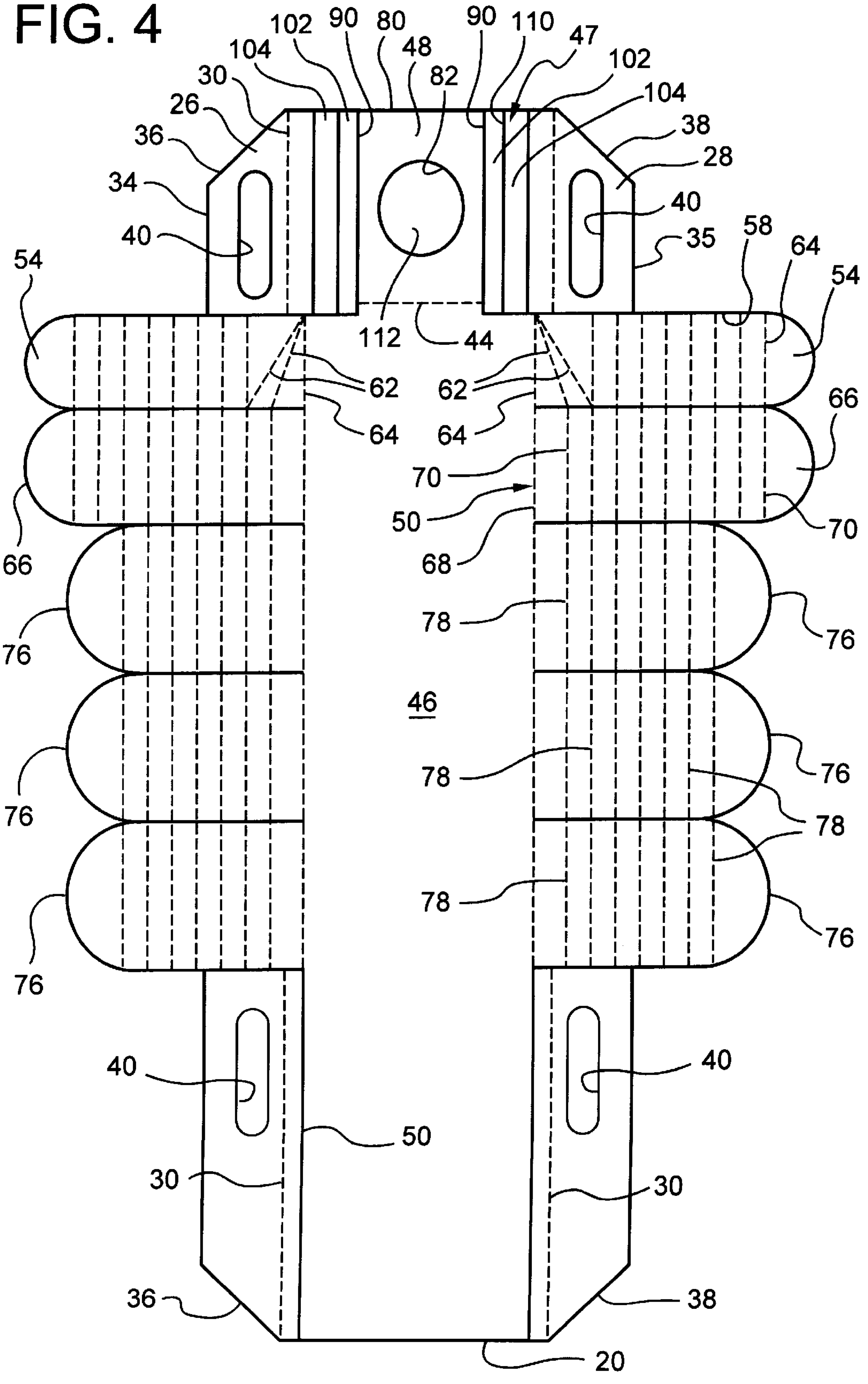
FIG. 4 is a top plan view of the backboard of FIG. 1 showing the arms in the extended position.

The base 12 has a generally rectangular configuration as shown in FIG. 4 with a center panel 16. The center panel 16 includes a first longitudinal end 18 and a second longitudinal end 20. The first longitudinal end 18 in the embodiment illustrated forms a head portion of the backboard 10 and the second longitudinal end 20 forms a foot portion. The center panel 16 also has a generally rectangular configuration and includes a first side edge 22 and a second side edge 24. A first side panel 26 is attached to the first side edge 22 and a second side panel 28 is attached to the second side edge 24. Each of the side panels 26 and 28 are coupled to the respective side edge of the center panel 16 by fold lines 30 and 32, respectively. The side panels 26 and 28 have an overall length substantially equal to the length of the center panel 16 and have a width of about 3–4 inches to provide adequate strength to the backboard 10. Fold lines 30 and 32 can be score lines by cutting partially through the material to allow the panels to fold easily. Generally, the thicker materials fold easier with a score line. In a preferred embodiment, the fold lines 30 and 32 are scored to form a substantially V-shaped recess to enable the side panels to fold until the faces of the recess mate.

As shown in FIGS. 1 and 4, each of the side panels 26 and 28 have a longitudinal side edge 34 and 35 and angled ends 36 and 38, respectively. The ends 36 and 38 of the side panels are angled from the fold line toward the outer side edges 34 and 35 so that the outer side edge is slightly shorter than the length of the center panel. In alternative embodiments, the ends 36 and 38 can be perpendicular to the longitudinal side edges so that the side panels have a generally rectangular shape.

A plurality of elongated slots 40 and 41 are spaced symmetrically along each of the side panels 26 and 28. The slots 40 and 41 are spaced apart a distance so that they do not significantly decrease the structural integrity of the of the side panels 26 and 28 or the backboard 10. The slots 40 and 41 have a length and width sufficient to allow a user to insert their fingers through the slot for lifting the backboard 10. In the embodiment illustrated, the slots 40 and 41 are positioned closer to the respective fold line of the panel, but can be positioned substantially in the middle of the side panels 26 and 28 between the inner and outer side edges. In the embodiment illustrated, six slots 40 are provided and uniformly spaced along the length of the side panels 26 and 28. In further embodiments, the slots can be non-uniformly spaced. The actual number of slots provided can vary depending on the length of the backboard 10 and the intended use.

Figure 5:
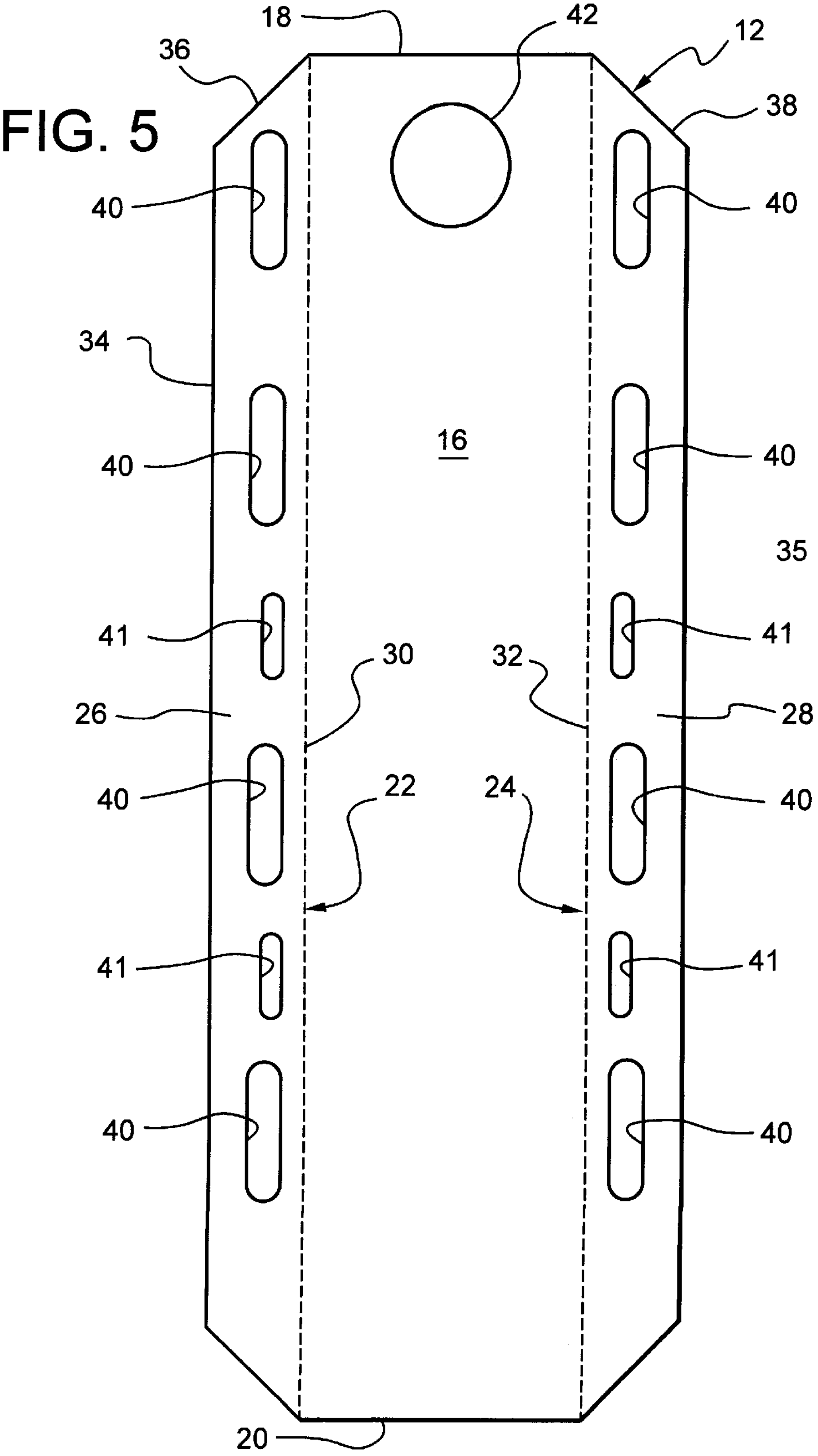
FIG. 5 is a top plan view of the blank of a base member for forming the backboard of FIG. 1.

As shown in FIG. 5, slots 40 are slightly larger than the slots 41. The smaller slots 41 are staggered with respect to the larger slots 40 and positioned generally toward the midsection of the base. The slots 41 are dimensioned to allow a user to grip the base and to receive a strap or other restraining device for securing a patient to the backboard 10. In further embodiments, the slots in the side panels 26 and 28 can be the same size.

Figure 2:
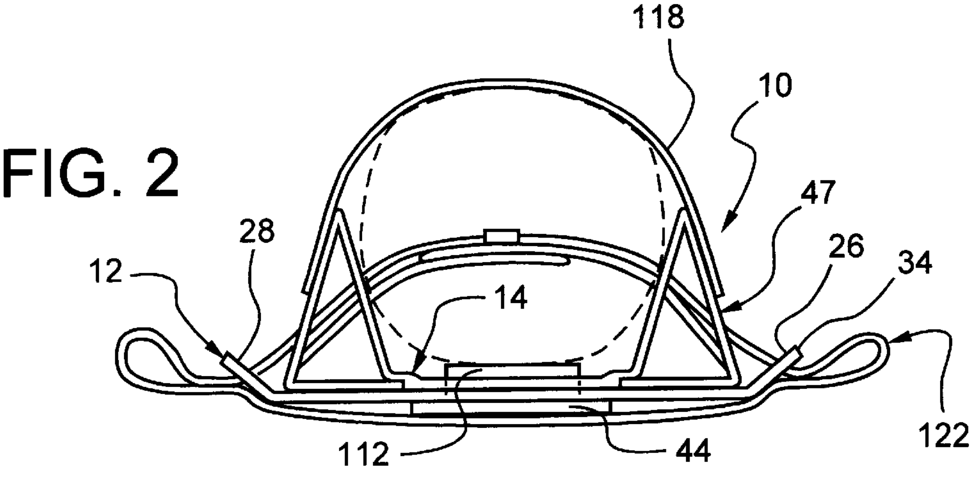
FIG. 2 is an end view of the backboard taken along lines 2—2 of FIG. 1.
Figure 3:
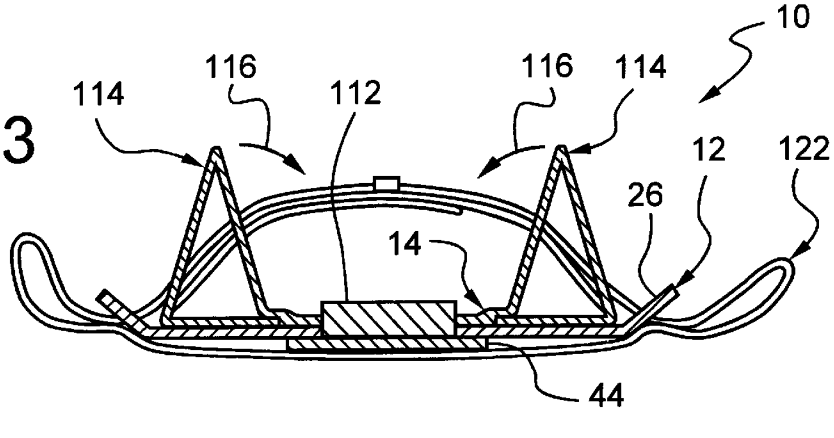
FIG. 3 is a cross-sectional end view taken along line 3—3 of FIG. 1.

A generally circular opening 42 is provided in the center panel adjacent the first end 18. As shown in FIGS. 2 and 3, a bottom panel 44 is attached to the bottom face of the center panel 16 to cover the circular opening 42. The bottom panel 44 has a generally square configuration and is dimensioned slightly larger than the diameter of the opening 42 to completely cover the opening 42. The bottom panel 44 can be attached to the center panel 16 by a suitable adhesive or other fastener.

Figure 6:
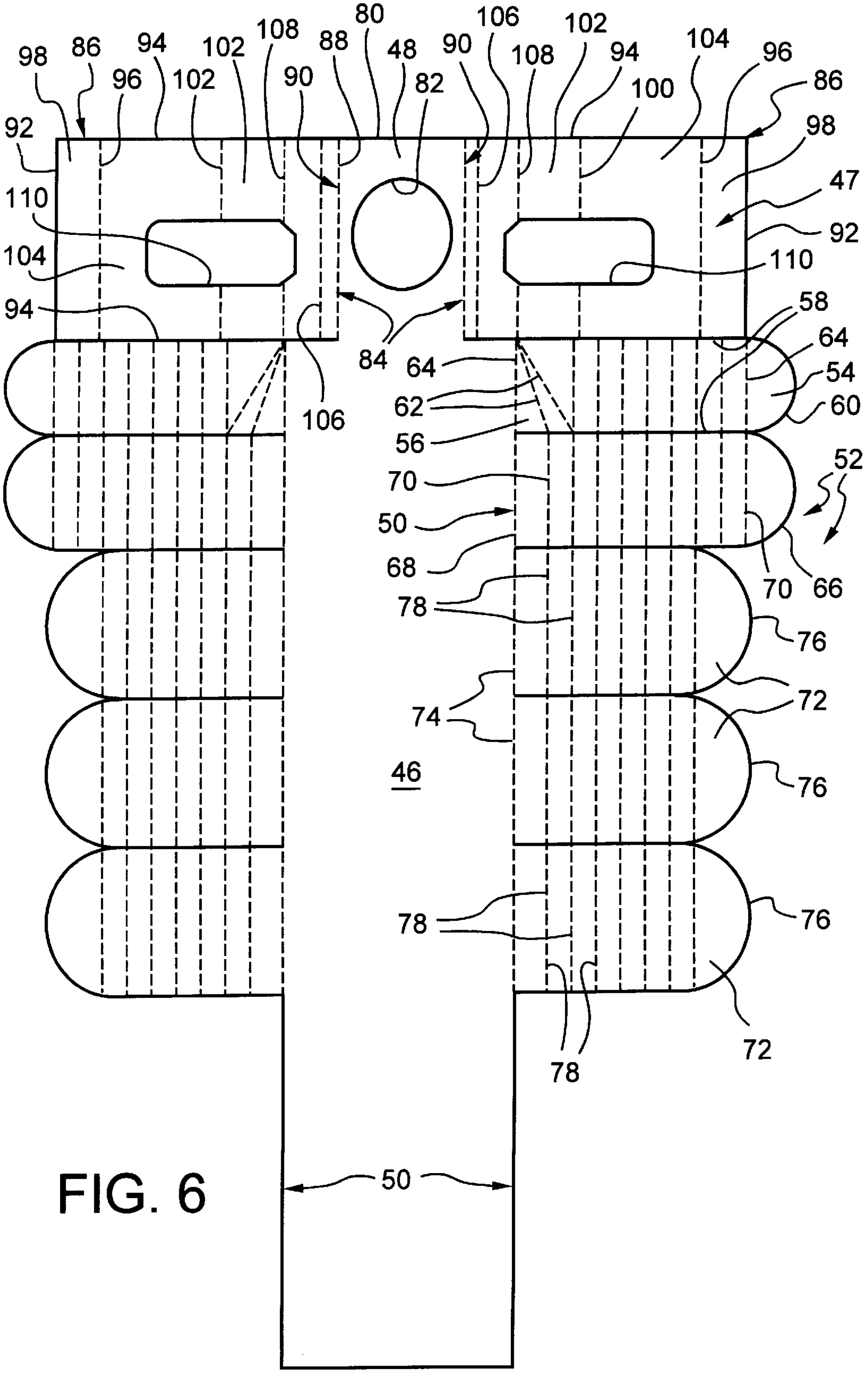
FIG. 6 is a top plan view of the blank for forming a patient supporting member of the backboard of FIG. 1.
Figure 7:
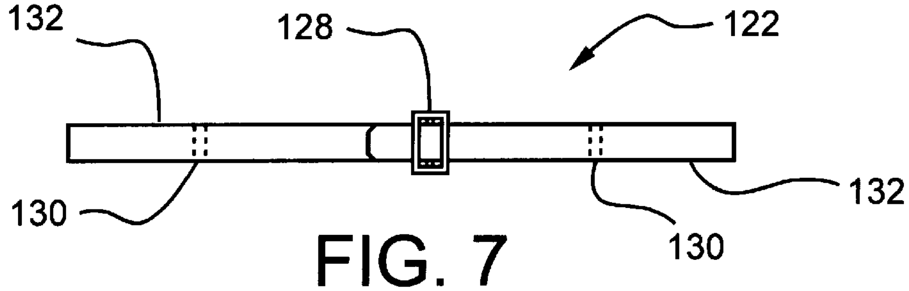
FIG. 7 is a front view of a belt for carrying the backboard of FIG. 1.
Figure 8:
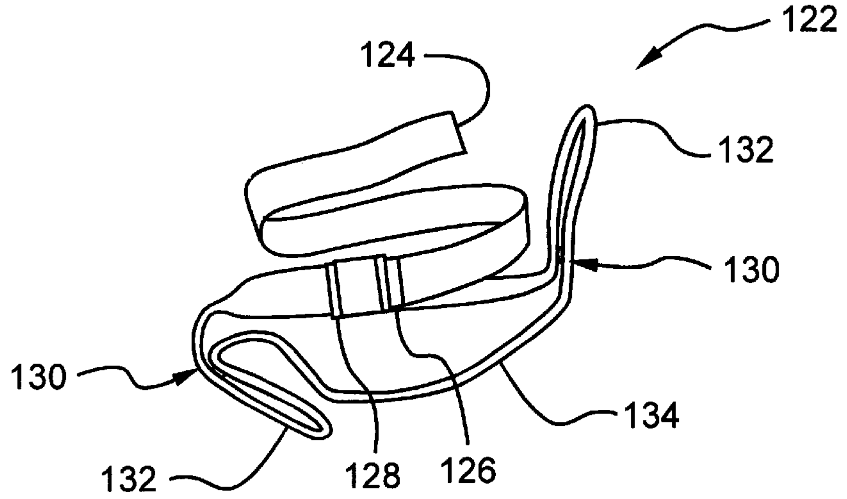
FIG. 8 is a perspective view of the belt for carrying the backboard of FIG. 1.

Referring to FIGS. 1, 4 and 6, the top panel 14 in the embodiment illustrated has a length substantially equal to the length of the base 12. The top panel 14 includes a generally rectangular center panel 46 and a head supporting member 47 having a center head panel 48. The center panel 46 in the embodiment illustrated in FIG. 1 has a length extending to the second end 20 of the base 12. In alternative embodiments, the center panel 46 can have a length less than the length of the base 12 depending on the strength required for the backboard 10. The center panel 46 and the head panel 48 in preferred embodiments are coupled to the base 12 by a suitable adhesive to form a unitary structure, although various mechanical fasteners such as staples can be used. Metal fasteners are generally less preferred since the metal interferes with the X-ray image. In the illustrated embodiment, the center panel 46 has longitudinal side edges 50 extending the length of the center panel 46. The center panel 46 of the top panel 14 has a width slightly less than the width of the center panel 16 of the base 12 to allow folding of the side panels 26 and 28 of the base 12 as discussed hereinafter in greater detail. In further embodiments, the center panel 46 of the top panel 14 can have a width equal to the width of the center panel 16 of the base 12.

As shown in FIG. 4, a plurality of arms 52 are coupled to the center panel 46 of the top panel 14. A first arm 54 has a generally elongated shape having an inner edge 56 coupled to each of the side edges 50 of the center panel 46 adjacent the head panel 48 by a fold line 64. The first arm 54 has side edges 58 extending substantially perpendicular from the inner edge 56 to a curved outer edge 60. The first arm 54 includes at least one fold line 62 extending diagonally from the corner 55 of the first arm 54 adjacent the head panel 48 and extending between the side edges 58. In the embodiment illustrated, two diagonal fold lines 62 are provided. A plurality of spaced apart fold lines 64 are formed parallel to the longitudinal axis of the center panel 46.

A second arm 66 is coupled to the side edge 50 of the center panel 46 by a fold line 68. The second arm 66 has a length substantially equal to the length of the first arm 54 in the illustrated embodiment. Preferably, the second arm 66 has a width slightly greater than the width of the first arm 54. A plurality of intermediate fold lines 70 are provided in a spaced apart relationship along the second arm 66 and extend generally parallel to the first fold line 68. As shown, the second arm 66 is formed adjacent the first arm 54.

At least one third folding arm 72 is provided adjacent the second arm 66 and is coupled to the center panel 46 by a fold line 74. In the embodiment illustrated, three of the third arms 72 are illustrated, although the actual number can vary depending on the needs of the device. The third arm 72 has a curved outer end 76 and a plurality of spaced apart fold lines 78 extending parallel to the first fold line 74. The third arm 72 has a length slightly less than the length of the second arm 66.

Preferably, the length of the arms 54, 66 and 72 are sufficient to be folded over a patient lying on the center panel 46. The fold lines formed in the arms allow the arms to conform easily to the contour of the patient. The diagonal fold lines 62 in the first arm 54 enable the first arm to be folded diagonally toward the second end 20 of the base 12 as shown in FIG. 1. The actual number of fold lines formed in the arms can vary depending on the actual length of the arms and the stiffness of the material from which the backboard is constructed.

The head panel 48 is integrally formed with the center panel 46 and has a width slightly less than the width of the center panel 46. The head panel 48 has a top edge 80 that extends to the first end 18 of the base 12. A circular opening 82 is formed in the head panel 48 and is superimposed with the circular opening 42 of the center panel 16 of the base 12.

The head panel 48 includes side edges 84 extending substantially parallel to the side edges 50 of the center panel 46. A foldable head supporting flap 86 having a generally rectangular shape is coupled to each of the side edges 84 along a fold line 88. Each flap 86 has an inner edge 90 and an outer edge 92 and side edges 94. A fold line 96 is spaced from the outer edge 92 to define an end tab 98. An intermediate fold line 100 extends parallel to the fold line 96 to form an inner panel 102 and an outer panel 104. The inner panel 102 includes a first fold line 106 extending parallel to the fold line 100. In the embodiment illustrated, the first fold line 106 is spaced close to the fold line 88 and a second fold line 108 is formed at about a midpoint between the fold line 88 and the fold line 100. In the embodiment illustrated, an opening 110 is formed in the flap 86 extending between the inner panel 102 and the outer panel 104. The opening 110 is dimensioned to provide an open area in a center region of the flaps without sacrificing the structural integrity of the flaps and the ability of the inner and outer panels to support a patient's head.

As shown in FIGS. 2 and 3, the inner panel 102 is folded upwardly along the fold line 88 and the outer panel 104 is folded downwardly along fold line 100 with respect to the plane of the inner panel 102 to form an inverted substantially V-shaped supporting structure. The end tab 98 is folded along fold line 96 and is attached to the center panel 16 of the base 12 by a suitable adhesive or mechanical fastener. In the embodiment illustrated, the end tab 98 is folded inwardly with respect to the outer panel 104. In alternative embodiments, the end tab 98 can be folded outwardly with respect to the outer panel 104. In one embodiment, the tab 98 is permanently fixed to the base 12. In further embodiments, the tab 98 can be removably coupled to the base 12 by a fastener, such as a hook and pile type fastener.

The backboard 10 in preferred embodiments of the invention is formed from an assembly of the top panel 14 and the base 12. As shown in FIG. 5, the base 12 is in the form of a blank cut from a single sheet of suitable material such as corrugated cardboard. As shown in FIG. 6, the top panel 14 is formed as a blank cut from a single sheet of material. The blanks can be cut by a suitable die cutting apparatus. Generally, the sheet material used for forming the base 12 has a thickness to provide the necessary rigidity to be able to support the weight of a patient. The sheet material used to form the top panel 14 can be thinner than the material used for the base 12. In preferred embodiments, the sheet material used to form the top panel 14 has a sufficient thickness to provide the necessary strength to the arms and the center panel while allowing the arms to be sufficiently flexible to fold and conform to the shape of a patient on the backboard 10.

Referring to FIGS. 2 and 3, a flexible cushion material 112 is positioned in the circular opening 82 of the top panel 14 and is attached to the bottom panel 44 by a suitable adhesive. The cushion material 112 has a shape to conform to the shape of the opening 82 and has a thickness to extend above the surface of the head panel 84 as shown. The cushion 112 preferably has a thickness to comfortably support the head of a patient. By placing the cushion material 112 in the openings and securing to the bottom panel 44, the cushion material is able to compress by the weight of the patient's head and lower the head in relation to the spine. Thus, the back of the patient's head can be received in the openings to tilt the head back with respect to the spine to maintain spinal alignment and proper airway position. The position of the head will depend on the weight of the patient and the compressibility of the cushion material.

The flexible arms of the top panel 14 can be folded inwardly in an overlapping manner onto the center panel 46 during storage. Alternatively, the arms can be folded outwardly in the plane of the center panel 46 so that the backboard is substantially flat. It is generally preferred to fold the arms inwardly to reduce the overall storage space required for the backboard. The inner panel 102 and the outer panel 104 of the flap 86 in the assembled device form a substantially inverted V-shape head support 114. The head support 114 can be folded inwardly in the direction of arrows 116 as shown in FIG. 3 so that the inner panel 102 folds along fold lines 106 and 108 to enable the head support 114 to lay substantially flat during storage.

During use, the head supports 114 are folded upwardly to the position shown in FIG. 2 and the arms are folded outwardly from the center panel 46 as shown in FIG. 4. The backboard 10 is placed under a patient with the patient's head positioned on the cushion 112 between the head supports 114. The fold lines 106 and 108 of the inner panel 102 enable the inner panel to conform to the contour of the patient's head so that the head supports 114 contact both sides of the patient's head to prevent or resist twisting and lateral movement of the head. The patient's ears are accommodated by the aperture 110 in the head support 114 so that the head supports engage the jaw and side of the patient's head. An adhesive tape 118 is generally secured to the outer panel 104 and extended across the area of the patient's forehead and the area of the patient's chin to secure the head supports 114 together and prevent movement of the head supports 114 with respect to each other. The first arms 54 are folded inwardly along the diagonal fold lines 62 so that the arms 54 cross over the patient's chest area. The second arm 66 and the third arm 72 are folded along the fold lines over the patient's torso and generally conform to the contour of the patient. The arms are held in place by a suitable securing device 120. The securing device 120 can be a belt, tape or other fastening device.

The fold lines 30 and 32 of the base 12 allow limited pivoting movement of the side panels 26 and 28 to the position shown in FIG. 2. During storage, the side panels 26 and 28 lay flat in the plane of the center panel 16. The fold lines 30 and 32 are preferably scored along the top face to form a substantially V-shaped recess along the fold line. This enables the side panels 26 and 28 to fold along the fold line to close the V-shaped recess providing limited pivotal movement of the side panels and enable the side panels 26 and 28 to assume an inclined position with respect to the center panel 16. This allows the user to place their hands easily under the side panels 26 and 28 to grip the slots 40 for lifting the backboard 10. Preferably, the backboard 10 is formed from corrugated cardboard so that an X-ray image of the patient can be taken while secured in the backboard without interference from the backboard materials. The tape and straps used to secure the patient to the backboard can be cut or otherwise removed so that the backboard 10 can be separated from the patient.

In a preferred embodiment of the invention, the securing device 120 is a belt 122 having a first free end 124 and a second end 126 having a buckle 128. The buckle 128 is able to receive the free end 124 to adjust the working length of the belt 122. The buckle 128 is a conventional clasp or snap-type buckle having a spring biased catch for rapid coupling and release. The belt 122 is secured together at a point 130 by stitching, adhesive or other fastener to form a closed loop 132 and a back portion 134. In the embodiment illustrated, two closed loops 132 are formed, although additional loops can be provided as needed. The loops 132 preferably have a length to allow a user to easily grip the loop. In a further embodiment, the loops can be formed from a separate piece of material that is attached to the belt 122.

Referring to FIGS. 2 and 3, the belt 122 is passed under the backboard 10 with the back portion 134 positioned below the base 12. The loops 132 are positioned adjacent the side panels 26 and 28 and the free ends of the belt 124 and 126 are passed through a selected slot 40 or 41 and are passed over the arms 54 of the backboard 10 and secured together by the buckle 128. The ends of the belt are adjusted by the buckle 128 to secure the patient to the backboard. In preferred embodiments, the back portion 134 of the belt 122 has a length substantially equal to the spacing between the slots 40 as measured along the bottom surface of the base 12. In this manner, the user can grip the loops 132 and lift the backboard 10 without altering the tension of the belt across the top portion of the backboard.

Figure 9:
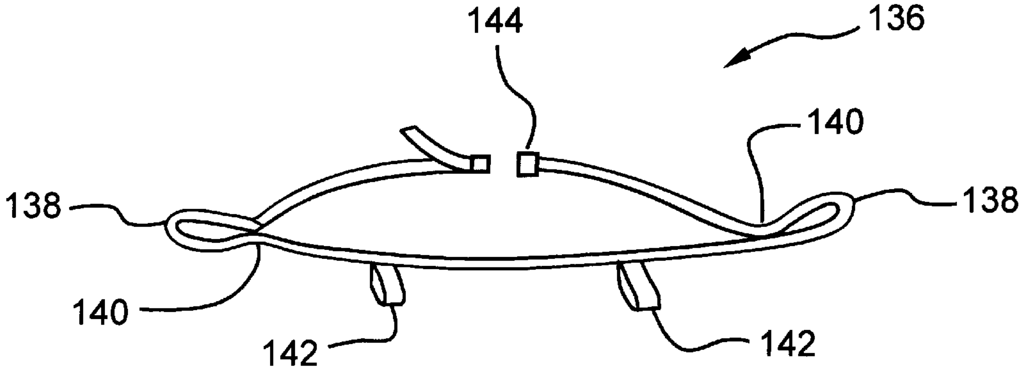
FIG. 9 is a top view of the belt in a further embodiment of the invention.

Although the belt 122 is illustrated for carrying the backboard 10 and securing the arms 54 of the top panel 14 over the patient, the belt 122 can be used independently of the backboard. As shown in FIG. 9, a belt 136 can include closed loops 138 formed by stitching portions of the belt together at a point 140. Loops 142 are formed from a separate piece of material that can be attached to the belt 136 by stitching or other mechanical fastener. A suitable buckle 144 is included to secure the free ends of the belt together. The belt 136 can then be used as a carrying harness by lifting on the loops 136 and 138 to assist in carrying a person. When the belt is intended for use in carrying a person, it is generally preferred to have the loops 138 formed along the back portion to provide an additional loop for carrying or lifting the person.

Although various preferred embodiments of the invention have been selected to illustrate the invention, it will be apparent to one skilled in the art that various additions and modifications can be made to the backboard without departing from the invention as defmed in the appended claims.

What is claimed is:

1. A backboard support comprising:

a substantially planar base member having a rigid center panel with a longitudinal dimension, a first longitudinal end, a second longitudinal end, a first side edge, and second side edge, said base further having a first side panel pivotally coupled to said first side edge, and a second side panel pivotally coupled to said second side edge; and a plurality of flexible arms coupled to said planar base and being hinged thereto along each of said first and second side edges and having a length to overlie a patient on said support for securing said patient on said support.

2. The support of claim 1, wherein said flexible arms are positioned on said planar base whereby said arms overlie one another in a patient securing position.

3. The support of claim 1, further comprising a plurality of said arms on said planar base at said first and second side edges and being positioned adjacent each other along said longitudinal dimension of said base, and wherein each of said arms has a length to overlap with an arm on an opposite side edge.

4. The support of claim 1, further comprising a head-supporting member for supporting a patient's head and resisting lateral or twisting movement of a patient's head with respect to said base.

5. The support of claim 4, wherein said head-supporting member includes first and second upright members for engaging opposite sides of a patient's head.

6. The support of claim 5, wherein each of said upright members include an inner panel for engaging a respective side of a patient's head and an outer panel for supporting said inner panel in a substantially upright position, said inner panel having a first end coupled to said base and having a second outer end, said outer panel having a first end coupled to said base and having a second end coupled to said second outer end of said inner panel.

7. The support of claim 6, wherein said upright members are movable from a collapsed position to an upright position.

8. The support of claim 7, wherein said upright members are foldable from said collapsed position to said upright position.

9. The support of claim 1, wherein said first and second side panels of a said base have at least one aperture dimensioned for gripping and lifting said support.

10. The support of claim 9, comprising a plurality of said apertures in said first and second side panels and spaced apart along said longitudinal dimension.

11. The support of claim 1, wherein each of said flexible arms includes at least one fold line whereby said arms are able to conform to the contour of a patient.

12. The support of claim 1, further comprising a cushion head support on said base.

13. The support of claim 12, wherein said head-supporting member includes a center panel coupled to said base, and said support further comprises a bottom panel coupled to a bottom side of said base, wherein said base and said center panel of said head-supporting member each include an aperture overlying said bottom panel and said cushion head support is positioned in said apertures and is coupled to said bottom panel.

14. The support of claim 1, further comprising a lifting strap encircling said base, said strap including free ends and a coupling member for coupling said free ends together around said base.

15. The support of claim 14, wherein said strap includes at least one closed loop formed therein.

16. The support of claim 1, wherein said first and second side panels are coupled to said center panel along a score line whereby said side panels are pivotable about a limited degree of movement.

17. A backboard support for carrying a patient, comprising:

- a planar base having a longitudinal dimension with first and second longitudinal ends and first and second side edges, wherein said planar base includes a center panel having a top face, first and second longitudinal side edges and a first side panel coupled to said first side edge of said center panel and a second side panel coupled to said second side edge of said center panel;
- a patient supporting panel having a longitudinal dimension with a first and a second longitudinal end and a first and a second side edge, said patient supporting panel being coupled to said top face of said base; and
- at least one arm coupled to each of said first and second side edges of said patient supporting panel and being hinged thereto, said arms having a length for overlying a patient on said support.

18. The support of claim 17, wherein said patient supporting panel has a width less than a width of said base.

19. The support of claim 18, wherein said first and second side panels are hinged to said center panel of said base.

20. The support of claim 19, wherein said first and second side panels are coupled to said center panel of said base by score lines.

21. The support of claim 18, wherein said first and second side panels include a plurality of apertures spaced along the longitudinal dimension of each of said side panels, said apertures being dimensioned to grip said side panels by a user.

22. The support of claim 17, further comprising a head-supporting member for supporting a patient's head and resisting lateral movement of a patient's head with respect to said base.

23. The support of claim 22, wherein said head-supporting member is integrally formed with said patient supporting panel.

24. The support of claim 22, wherein said head-supporting member includes first and second upright members for engaging opposite sides of a patients head.

25. The support of claim 24, wherein each of said upright members include an inner panel for engaging sides of a patient's head and an outer panel for supporting said inner panel in a substantially upright position, and wherein said inner panel and said outer panel are coupled together.

26. The support of claim 25, wherein said upright members are movable from a collapsed position to an upright position.

27. The support of claim 25, wherein said head supporting member includes a center panel dimensioned for supporting a patient's head, said center panel being coupled to said base, and second inner panels of said head supporting member being coupled to said center panel of said head supporting member.

28. The support of claim 17, wherein each of said arms includes at least one fold line whereby said arms are able to conform to the contour of a patient.

29. The support of claim 17, further comprising a cushion head support on said base.

30. The support of claim 17, wherein said first and second side panels of said planar base extend substantially the length of said planar base.

31. A backboard support for carrying a patient comprising:

- a planar base having a longitudinal dimension with first and second longitudinal ends and first and second side edges;
- a patient supporting panel having a longitudinal dimension with a first and a second longitudinal end and a first and a second side edge, said patient supporting panel being coupled to said base; and
- a plurality of arms on each of said first and second side edges of said support panel and spaced adjacent each other along said longitudinal dimension of said support panel, and wherein each of said arms has a length to overlap with an arm on an opposite side edge of said support panel and overlying a patient on said support.

32. The backboard support for carrying a patient comprising;

- a planar base having a longitudinal dimension with first and second longitudinal ends and first and second side edges;
- a patient supporting panel having a longitudinal dimension with a first and a second longitudinal end and a first and a second side edge, said patient supporting panel being coupled to said base;
- at least one arm coupled to each of said first and second side edges of said patient supporting panel and being hinged thereto, said arms having a length for overlying a patient on said support; and
- a lifting strap encircling said base and support panel, said strap including free ends and a coupling member for coupling said free ends together.

33. The support of claim 32, wherein said strap includes at least one closed loop.

34. A backboard support for carrying a patient comprising:

- a planar base having a longitudinal dimension with first and second longitudinal ends and first and second side edges;
- a patient supporting panel having a longitudinal dimension with a first and a second longitudinal end and a first and a second side edge, said patient supporting panel being coupled to said base;
- said base and said patient supporting panel including an aperture at one end of said support, and said support including a bottom member attached to a bottom face of said base covering said aperture in said base and having a resilient cushion coupled to said bottom member and being positioned in said apertures in said base and patient supporting member.

35. An assembly for forming a backboard support comprising;

a first blank having a longitudinal dimension with longitudinal ends and first and second side edges; and a second blank having a center panel with a longitudinal dimension and having longitudinal ends and first and second side edges, and a plurality of arms spaced along said side edges and being coupled to each of said side edges of said center panel along a fold line.

36. The assembly of claim 35, wherein said first blank has a center panel with a first side panel coupled to a first side edge of said center panel by a fold line and a second side panel coupled to a second side edge of said center panel by a fold line.

37. The assembly of claim 36, wherein said center panel includes an aperture at one end.

38. The assembly of claim 36, wherein each of said side panels include a plurality of spaced apart apertures dimensioned for gripping said side panel.

39. The assembly of claim 35, wherein each of said arms have a plurality of fold lines extending substantially parallel to said longitudinal dimension of said center panel of said second blank.

40. The assembly of claim 35, wherein said second blank includes a head panel coupled to said center panel and having first and second parallel slide edges extending parallel to said side edges of said center panel, said head panel including a first arm coupled to said first edge by a first fold line and a second arm coupled to said second edge, said arms being coupled to said head panel by a first fold line, each said arms including a second fold line extending parallel to said first fold line and forming an inner panel and an outer panel.

41. The assembly of claim 40, wherein each of said arms include an outer edge and a third fold line parallel to said first fold line, said third fold line being spaced from said outer edge to form an end tab.

42. The assembly of claim 41, wherein each of said arms further include a fourth fold line parallel to said first fold line and positioned between said first and second fold lines.

43. The assembly of claim 40, wherein each of said arms include a central aperture.

44. An assembly for forming a backboard support comprising:

a first blank having a longitudinal dimension with longitudinal ends and first and second side edges;

a second blank having a center panel with a longitudinal dimension and having longitudinal ends and first and second side edges, and a plurality of arms spaced along said side edges and being coupled to each of said side edges of said center panel along a fold line; and a first arm coupled to each of said first and second side edges of said center panel along a respective first fold line, each of said first arms having at least one second fold line extending in a generally diagonal direction with respect to said first fold line and at least one third fold line extending in a direction substantially parallel to said first fold line.

* * * * *